United States Patent [19]

Isaac

[11] 4,004,976

[45] Jan. 25, 1977

[54] PROCESS FOR RECOVERING THE MAIN SAPOGENINS FROM THE ROOTS OF RHIZOMES OF HELLEBORUS

[75] Inventor: Otto Isaac, Bruchkobel, Germany

[73] Assignee: Deutsche Gold- und Silber-Scheideanstalt vormals Roessler, Frankfurt, Germany

[22] Filed: Apr. 7, 1975

[21] Appl. No.: 565,698

[30] Foreign Application Priority Data

Apr. 8, 1974 Germany .......................... 2416979

[52] U.S. Cl. .................................................. 195/2
[51] Int. Cl.$^2$ ......................................... C12D 13/08
[58] Field of Search .......................... 195/2.4, 51 R; 260/210.5

[56] References Cited

UNITED STATES PATENTS

3,420,740  1/1969  Kawasaki ............................... 195/2

OTHER PUBLICATIONS

Linde et al., "Uber Sapogenine", Helv. Chim. Acta, vol. 54 (1971) pp. 1703–1708.
Dixon et al., "Enzymes", 2nd Edition, Academic Press, 1964, pp. 740–745.

Primary Examiner—R. B. Penland
Attorney, Agent, or Firm—Cushman, Darby & Cushman

[57] ABSTRACT

The main sapogenins in the roots and rhizomes of Helleborous species are recovered by treating the roots and/or rhizomes or drugs or extracts made therefrom with cellulase, hemicellulase or $\beta$-glucosidase.

8 Claims, No Drawings

PROCESS FOR RECOVERING THE MAIN SAPOGENINS FROM THE ROOTS OF RHIZOMES OF HELLEBORUS

REFERENCE TO RELATED CASES

This application is related to my companion case Ser. No. 565,697 filed on even date and corresponding to German application P 24 16 978.6. The entire disclosure of the companion case is hereby incorporated by reference and relied upon.

The roots and rhizomes of Helleborus species contain a saponin mixture whose main sapogenin has the structure of a spiro-5,25(27)-diene-1β,3β,11α-triol (formula I).

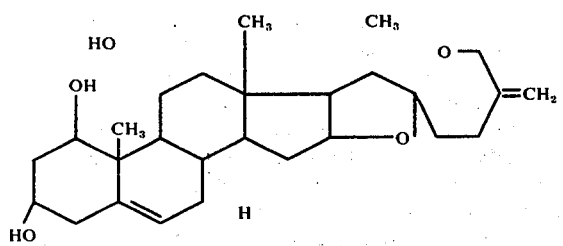

According to Linde, Helv. Chim. Acta Vol. 54, pages 1703–1708 with specific reference to page 1707, to recover this sapogenin rhizomes and coarsely pulverized roots of Helleborus species are taken up in water and left to an autofermentation for 22 days. Subsequently, the drug residue is filtered off and extracted with aqueous alcohol. The residue of the alcoholic extract is chromatographed on silica gel. The sapogenin fraction is recrystallized from methanol-acetone. By preparative thin layer chromatography in the system diisopropylether-ethanol (92:8 by volume) there is finally obtained the pure sapogenin, M.P. 236°–240° C. In the specific example in Linde employed Helleborus odorus but mention is made that Helleborus niger was also used in similar manner to obtain the same sapogenin of formula I. The entire disclosure of Linde is incorporated herein by reference and relied upon.

Rhizomes are underground, more or less thickened axis of the shoot which plainly differs from roots through the presence of mostly scaly lower leaves and through their organization. Webster's Seventh New Collegiate Dictionary defines rhizome as "a somewhat elongate usually horizontal subterraneous plant stem that is often thickened by deposits of reserve food material, produces shoots above and roots below, and is distinguished from a true root in possessing buds, nodes, and usually scalelike leaves."

It has now been found that this main genin of the sapogenin mixture which is contained in the roots and rhizomes of Helleborus species can be recovered in a simpler and quicker manner if the roots and rhizomes of Helleborus species or drugs or extracts obtained therefrom are treated with an enzyme mixture whose essential active components are cellulase, hemicellulase or β-glucosidase.

The enzyme treatment takes place in a customary manner. There is suitably maintained a temperature between 20° and 50° C. A temperature between 30° and 40° C. is generally especially favorable.

According to the process of the invention there can be employed directly the pulverized roots and rhizomes of Helleborus species or there can be used an extract recovered in customary manner or a drug from Helleborus species which has been worked up and pulverized in customary manner. The treatment can be carried out in solution, in suspension or in form of a mash. Thus, for example, the enzyme can be added to the autolysate of roots and rhizomes of Helleborus species. The autolysis or autofermentation can be carried out for example by pulverizing fresh plant parts and allowing the thus obtained material to stand for a period of time (for example 2–25 days) at temperatures between 18° to a maximum of 60° C., in a given case after adding water and with occasioned stirring. Also dried plant parts can be stirred with water so long as their fermentative activity is maintained, and be autofermentated. The enzyme can be added either at the beginning of the autofermentation process or also during this process with equally satisfactory results.

However, it is also possible to first produce an extract in known manner from the roots and rhizomes or a drug produced therefrom and treat this, in a given case after a conventional preliminary purification, with the enzyme. For this purpose suitably the roots or rhizomes or drug first is extracted with alcohol (ethyl alcohol) or an alcohol water mixture containing a maximum of 50% water. The thus obtained extract is subsequently extracted by shaking with organic solvents, e.g., water immiscible organic solvents, for example, aromatic hydrocarbons, e.g. benzene, toluene, xylene, halohydrocarbons, e.g. chloroform, carbon tetrachloride, 1,2-dichloroethane, or halo-hydrocarbon-alcohol mixtures as for example chloroform-ethanol. If halohydrocarbon-alcohol mixtures are used the mixing ratio is preferably 2:1. However, it is favorable if the organic extract obtained is prepurified.

Such a preliminary purification can take place in customary manners therefore. However, it can also take place for example by chromatographization of a silica gel whereby as silica gel there is used a synthetically produced highly porous, amorphous, silica in the form of hard particles with a particle size of 0.15 to 10 mm. Especially favorable is a particle size of 0.15 to 0.30 mm. The water content of this silica, for example, can amount to 10%. The specific surface area can be from 300 m² to 650 m²/g. Generally the surface area is about 400 m²/g. The apparent density can be from 400 to 750 g/l. An apparent density (bulk density) of 450 to 500 g/l is propitious.

As eluting agents for the silica chromatography of the organic extracts of the roots and rhizomes of Helleborus species there may be mentioned aliphatic halohydrocarbons, e.g. methylene chloride, chloroform, carbon tetrachloride, 1,2-dichloroethane, trichloroethylene, ethylene dibromide, ethylene tetrachloride, mixtures of aliphatic halohydrocarbons (e.g. those just mentioned) with aliphatic alcohols, e.g. alkanols such as methanol, ethanol, propanol, isopropanol or butanol, esters of aliphatic acids with aliphatic alcohols, e.g. methyl acetate ethyl acetate, butyl acetate, ethyl propionate, ethyl formate, methyl butyrate, ester-alcohol mixtures (such as mixtures of the above-mentioned carboxylic acid esters and alcohols), ester-alcohol-water mixtures (such as mixtures of the above-mentioned carboxylic acid esters and alcohols with water, benzene, halobenzenes, e.g. chlorobenzene, fluorobenzene, bromobenzene and o-dichlorobenzene, alkyl benzenes, e.g. toluene, o-xylene, m-xylene, p-xylene, ethyl benzene and cumene, alkyl benzene-alcohol mixtures (such as mixtures of the above-mentioned alkyl benzenes and alcohols, ester-pyridine mixtures (such as mixtures of the above-mentioned carboxylic acid esters with pyridine), halohydrocarbon-pyridine mixtures (such as mixtures of the above-mentioned halohydrocarbons with pyridine), halohydrocarbon-alcohol-pyridine mixtures (such as mixtures of the above-mentioned halohydrocarbons and alcohols with pyridine), ester-pyridine-water mixtures (such as mixtures of the above-mentioned carboxylic acid esters with pyridine and water), mixtures of benzene, halobenzenes and alkylbenzenes with pyridine (such as mixtures of benzene, the above-mentioned halobenzenes and the above-mentioned alkylbenzenes with pyridine), aliphatic ketones, e.g. acetone, methyl ethyl ketone and methyl butyl ketone, ketone-water mixtures (such as mixtures of the above-mentioned ketone with water, ketone-benzene mixtures (such as mixtures of the above-mentioned ketones with benzene, ketone-benzene-glacial acetic acid mixtures (such as mixtures of the above-mentioned ketones with benzene and acetic acid), etc. It is understood that other mixtures of the above-mentioned types of components are also possible. The optimum ratio of mixing the components can be readily ascertained in a separate preliminary test.

For example as the above-mentioned aliphatic liquids there can be used the lower molecular weight liquids which are customarily used as solvents. The term halogen means fluorine, chlorine and bromine, preferably fluorine and chlorine. Under alkyl benzenes these are included with lower alkyl groups. Examples are toluene, ethyl benzene, xylene and the others mentioned supra.

The prepurified and completely solvent-free saponin fraction is then incubated in water with the enzyme. The incubation can be carried out for example at a temperature of 20° to 50° C. For protection against bacterial decomposition toluene can be added (mostly in small amounts) to the incubate.

There can be used in the process of the invention the commercial cellulase, hemicellulase and β-glucosidase preparatives. Likewise, there can be used preparatives of the just named enzymes which have been produced according to known processes for such purpose from fungi, microorganisms (trichodermo viride, for example), protozoa, bacteria, insects, plants or invertebrate animals such as snails (edible snails) and worms (see Sumner et al., The Enzymes, Vol. 1, Part 2 ([195]) pages 729–731, the entire disclosure of which is hereby incorporated by reference and relied upon) and Ullmanns Enzyklopaedie der technischen Chemie, 3rd edition (1956) pages 391–396, the entire disclosure of which is hereby incorporated by reference and relied upon).

Examples of sources of cellulases include for example barley malt, potato sprouts, aspergillus oryzae, aspergillus niger, merulius lacrymans, myrothecium verrucaria, cellobacillus, cytophaga sp., plectridium cellulolyticum, eudiplodinium neglectum, trichomonas termopsidis, helix pomatia, bankia setacea, reticulitermes flaipes, termopsis angusticollis, cryptocercus punctulatus and stromatium fulvum.

The enzyme, as for example cellulase, is obtained if the culture medium or the aqueous myceltial extract of fungi is precipitated with alcohol (ethanol), acetone or salt. The crude enzyme can then be further purified, for example, on aluminum oxide. There should be used the freshest possible preparative which has not been stored for long. Stored preparatives should be kept cool and dry. Especially suitable are enzyme preparatives or enzyme concentrates of fungi or Aspergillus species such as *Aspergillus niger*, *Aspergillus oryzae*, *Aspergillus flavus*, *Aspergillus fumigatus*, *Aspergillys nidulans*. Especially favorable are preparatives or enzyme concentrates from *Aspergillus niger*.

It is necessary by preliminary tests to determine the activity of the enzyme and to ascertain the optimum reaction ratios and proportions in the conventional. Enzyme concentrates which consists, for example chiefly of cellulase, hemicellulase or β-glucosidase appear especially favorable. Frequently, such preparatives contain besides related enzymes such as pectinase, amylase, acid protease, xylanase cellobiase, glucoamylase, endopeptidases, lipase, pectinxylopolygalacturonase. It is likewise favorable if the enzyme preparatives according to the invention contain besides maceraingly acting enzymes (for example pectinglycosidase). Among other examples are highly purified products from Aspergillus species, which mainly consist of cellulase and hemicellulase and contain besides pectinase, amylase and acid protease (cellulosin preparatives).

Generally, the enzymatic reaction is ended after two days. With enzymes having higher activity, the reaction can be ended even earlier with enzymes having lower activity, however, the treatment can be carried out a considerably longer time.

The enzyme can be mixed either as such or in aqueous solution with the substrate.

The optimum pH value for the enzyme treatment is about 4.5 to 4.7. It is advantageous to stir the incubate or to keep it in motion in other ways.

The amount in which the enzyme is added depends on the activity of the enzyme and also on the substrate used. The enzyme, for example, can be added in very large excess. If, for example, a crude saponin fraction is added which, for example, is preliminarily purified in the manner given above, there can be added 5 to 100% of the enzyme preparative necessary according to the degree of purity determined by thin layer chromatography. If, for example, the drug is directly reacted or roots and rhizomes of Helleborus species then an amount between 1 and 10% based on the drug or the roots and rhizomes is sufficient.

The crude sapogenin resulting from the enzyme treatment can be further worked up according to the customary processes described in the literature. For example, there can be used the process of Linde set forth on page 1707 of the Linde article in Helv. Chim. Acta, Vol. 54, set forth previously. (Chromatography on $SiO_2$ having a particle size of 0.05 to 0.2 mm.)

However, especially desirable is a purification (for example by chromatography) of the crude sapogenin obtained with the help of silica gel with a particle size of 0.2 to 0.5 mm. As eluation agents there are especially suitable lower halogenated hydrocarbons such a methylene chloride and chloroform to which there can be added 1% and up of a lower aliphatic alcohol such as methanol or ethanol.

The thus obtained sapogenin can be recrystallized once from propanol-water.

It is possible according to the process of the invention to isolate the Helleborus-sapogenin in considerably greater amount than is possible by preparative thin layer chromatography.

As starting materials there can be used the known Helloborus species, for example *Helleborus foetidus L., Helleborus multifidus Vis., Helleborus niger L., Helleborus odorus Waldst. et Kit., Helleborus orientalis Lam., Helleborus purpurascens Waldst. and Kit., Helleborus viridis.*

Nothing was previously known of the physiological activity of the main sapogenin from the roots and rhizomes of Helleborus species. It has now likewise been found that the main genin recovered from Helleborussaponin has an ulcer healing activity. Furthermore, a muscle relaxing and central nervous system influencing activity has been established. The ulcer protective activity can be seen from the following table.

| Daily Dosage | Ulcer Protecting Effect |
| --- | --- |
| 50 mg/kg | 58% |
| 100 mg/kg | 78% |
| 200 mg/kg | 80% |

These tests were carried out according to the method of John and Adrian modified by Wilhelmi on the indometacin ulcer of rats (see Arneimittelforschung Vol. 19 (1969) pages 45 et seq.)

The determination is carried out in the following manner.

Albino rats of the strain SIV 50 (S. Ivanovas, Kisslegg/Allgau) having an initial weight of 250 to 300 grams were held in controlled temperature rooms at 20° to 22° C. in wire cages (Ebeco, Type 3 double width) on a standard diet (Altromin). After 48-hour feeding intervals the animals received 20 mg/kg rat of indometacin in 1.5% tragacanth (1 ml tragacanth solution per 100 grams of rat) applied intragastrally.

One hour after giving the indometacin there was dispensed orally to the animals the test substance. The rats remain otherwise fasting (water ad libitum).

Twenty-four hours after giving the indometacin the animals were killed with $CO_2$. The stomach was resected, opened along the great curvature and washed under flowing water.

The ulcerative changes appear as dark, point or stria shaped spots on the mucosa. The evaluation was done according to the method of Munchow, Arneimittelforschung Vol. 4 (1954) pages 341–344.

The compound of the invention is suitable for the production of pharmaceutical preparations. Medicines containing as the active ingredient the compound of the invention, in a given case in admixture with other pharmacologically or pharmaceutically active materials. The production of the medicines can take place using the customary pharmaceutical adjuvants.

The pharmacological and galenical handling of the compound of the invention is carried out according to conventional standard methods. For example, the active material and adjuvant or carriers are well mixed by stirring or homogenization (for example by means of colloid mills, ball mills), whereby generally here are employed temperatures between 20° and 80° C., preferably 20° to 50° C.

The medicine can be used, for example, orally, parenterally, rectally, vaginally, perlingually or locally.

Other medicinally active materials can also be added.

The compound of the invention shows a good antiulcer activity in indometacin ulcers of rats.

The antiulcer activity is comparable to the activity of the known medicine Biogastrone.

The lowest effective dosage in the above-mentioned animal experiments for example is 50 mg/kg orally.

As a general dosage range for the above-mentioned activity (animal experiments as above set forth) there can be employed for example 50 to 500 mg/kg orally.

The compound of the invention can be used in treating ulcus ventriculi, ulcus duodeni, gastritis, duodenitis, etc.

The pharmaceutical preparation generally contain between 1 and 50% of the active component of the invention although this can be varied.

The medicine containing the compound can be dispensed in the form of tablets, capsules, dragees or in liquid form. As liquid forms there can be used for example oily or alcoholic solutions as well as emulsions. The preferred forms of use are tablets which contain between 50 and 500 mg of the compound of formula I or solutions which contain between 0.5 and 10% of the active substance of formula I.

The individual dosages of the active component of the invention can be between 50 and 500 mg in orally administered medicines.

For example, it is recommended to use 1 to 5 tablets containing 50 to 500 mg of active substance 3 times a day.

The acute toxicity of the compound of the invention in the mouse (expressed by LD 50 mg/kg; method of Miller and Tainter; Proc. Soc. Exper. Biol. a. Med. Vol. 57 (1944) pages 261 et seq.) on oral application, for example, is above 6000 mg/kg.

Unless otherwise indicated all parts and percentages are by weight.

EXAMPLE 100 kg of roots and rhizomes of Helleborus viridis were comminuted, defatted with petroleum ether and subsequently exhaustively extracted with 80% aqueous ethanol. The residue of the ethanol extract was taken up in water and the solution extracted by shaking with chloroform/ethanol (2:1 by volume). The chloroform solution portion was chromatographed on a silica gel column with chloroform/methanol (9:1 by volume) and the fractions examined thin layer chromatographically Absorbent: silica gel for thin layer chromatography
Flowing agent: chloroform/methanol/water (35:25:10 by volume)
Detection: anisaldehyde/sulfuric acid/acetic acid (1:1:100 by volume)

The fractions were collected which essentially contained a brown colored material of average Rf-value (about 0.50) which is localized in the chromatogram between desglucohellebrin and hellebrin.

The residue of the combined fractions (2621 grams) was dissolved under reflux in 2.4 liters of methanol and 2.4 liters of water. After addition of 24 liters of tap water there was distilled off from the solution 4.8 liters of solvent.

After cooling, the solution was treated with 240 grams of a commercial cellulase (Rohm and Haas) as well as 100 ml of toluene and aged at 40° C. with occasional shaking. After about 48 hours the reaction was complete. The precipitate was filtered off with suction, washed with hot water and dried. Yield 1100 grams.

The dried precipitate was dissolved in methanol and dichloromethane (50:50 by volume) and the solution chromatographized with dichloromethane/methanol (increasing methanol concentration) on silica gel for column chromatography with a particle size of 0.2–0.5 mm.

The sapogenin fraction (736 grams) was dissolved in 5 liters of n-propanol and the solution treated with 30 liters of water. After 24 hours the crystals which separated were washed with propanol/water and dried.

Formula: $C_{27}H_{40}O_5$; M.P. 238° C; $[\alpha]_D^{20} = 86.93°$ C. (c = 1.1:pyridine).

The process can comprise, consist essentially of or consist of the steps set forth.

What is claimed is:
1. A process for the recovery of the main genin in the roots and rhizomes of a Helleborus species, said main genin having the formula

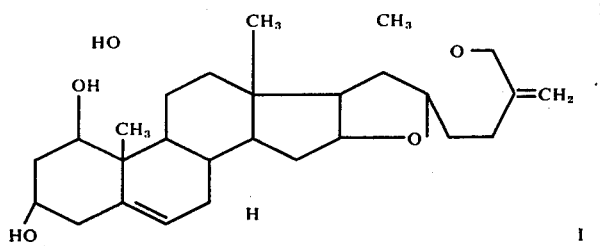

I comprising treating the roots, rhizomes or an extract containing said main genin with an enzyme which is cellulase, hemicellulase or β-glucosidase and recovering said main genin after the enzyme treatment.

2. A process according to claim 1 wherein the Helleborus species is Helleborus foetidus L.

3. A process according to claim 1 wherein the Helleborus species is Helleborus multifidus Vis.

4. A process according to claim 1 wherein the Helleborus species is Helleborus niger L.

5. A process according to claim 1 wherein the Helleborus species is Helleborus odorus Waldst. et Kit.

6. A process according to claim 1 wherein the Helleborus species is Helleborus orientalis Lam.

7. A process according to claim 1 wherein the Helleborus species is Helleborus purpurascens Waldst. and Kit.

8. A process according to claim 1 wherein the Helleborus species is Helleborus veridis.

* * * * *